United States Patent [19]

Baurain et al.

[11] Patent Number: 4,973,465
[45] Date of Patent: Nov. 27, 1990

[54] MICROCRYSTALS COMPRISING AN ACTIVE SUBSTANCE HAVING AN AFFINITY FOR PHOSPHOLIPIDS, AND AT LEAST ONE PHOSPHOLIPID, PROCESS OF PREPARATION

[75] Inventors: Roger Baurain, Wezembeek; Andre B. L. Trouet, Winksele, both of Belgium

[73] Assignee: Ire-Celltarg S.A., Fleurus, Belgium

[21] Appl. No.: 364,481

[22] Filed: Jun. 8, 1989

Related U.S. Application Data

[63] Continuation-in-part of Ser. No. 128,944, Dec. 4, 1987, abandoned.

[30] Foreign Application Priority Data

| Dec. 5, 1986 [FR] | France | 86 17116 |
| Feb. 19, 1987 [FR] | France | 87 02137 |
| Sep. 8, 1987 [FR] | France | 87 12424 |

[51] Int. Cl.$^5$ .................................... A01N 25/32
[52] U.S. Cl. ................... 424/406; 424/417; 424/498; 424/499; 424/502; 514/31
[58] Field of Search ............... 424/406, 417, 498, 499, 424/502

[56] References Cited

U.S. PATENT DOCUMENTS

| Re. 32,393 | 4/1987 | Wretlind et al. | 514/219 |
| 2,664,380 | 12/1953 | Vierling | 167/53 |
| 4,396,630 | 8/1983 | Riedl et al. | 424/502 |
| 4,647,586 | 3/1987 | Mizushima et al. | 514/532 |
| 4,687,762 | 8/1987 | Fukushima et al. | 514/34 |
| 4,727,077 | 2/1988 | Hega et al. | 514/274 |

OTHER PUBLICATIONS

"Characteristics of Drug-Phospholipid Coprecipitates I: Physical Properties and Dissolution Behavior of Griseofulvin-Dimyristoylophosphatidylcholine Systems", Journal of Pharmaceutical Sciences, vol. 73, #6, 6/84, pp. 757-761, S. Venkataram et al., Amer. Pharmaceutical Assoc., Wash.

*Primary Examiner*—William R. Dixon, Jr.
*Assistant Examiner*—David M. Brunsman
*Attorney, Agent, or Firm*—Fleit, Jacobson, Cohn, Price, Holman & Stern

[57] ABSTRACT

The present invention relates to microcrystals of a substance, which substance is insoluble in water and has an affinity for phospholipids, as well as a process for its preparation. According to the invention, one or more organic solvents are evaporated from a solution of phospholipids and substance, and the film obtained thereby, after evaporation of the one or more solvents, is suspended in an aqueous solution by vigorous stirring. The invention also relates to pharmaceutical compositions containing as active principle these microcrystals, particularly liquid pharmaceutical compositions packaged in injectable form or in sprayable form.

34 Claims, No Drawings

MICROCRYSTALS COMPRISING AN ACTIVE SUBSTANCE HAVING AN AFFINITY FOR PHOSPHOLIPIDS, AND AT LEAST ONE PHOSPHOLIPID, PROCESS OF PREPARATION

This application is a continuation-in-part of application Ser. No. 128,944, filed Dec. 4, 1987, abandoned.

BACKGROUND OF THE INVENTION

The present invention relates to lipid microparticles of crystalline appearance called microcrystals. It relates to microcrystals of a substance insoluble in water having an affinity for phospholipids, and at least one phospholipid.

The present invention relates also to a process for the preparation of microcrystals of a substance insoluble in water having an affinity for phospholipids. It relates to the microcrystals obtained, as well as to pharmaceutical compositions containing them.

GENERAL DESCRIPTION OF THE INVENTION

According to the invention there is provided a process for the preparation of microcrystals which is characterised in that it comprises the following steps:

a) evaporating the one or more solvents of a solution of phospholipids and of a substance which is insoluble in water and has an affinity for phospholipids; and b) suspending the film obtained by evaporation of the one or more solvents, in an aqueous solution by vigorous stirring.

In the present application, 'microcrystals' means lipid microparticles of crystalline appearance obtained particularly by the above process or a process derived therefrom, it being understood that the crystalline structure is not necessarily obtained in the strict sense of the word.

In this process, 'substance insoluble in water', must be understood to mean a substance which has little or no solubility in water and by 'substance having an affinity for phospholipids' is meant a chemical compound more particularly capable of interacting with phospholipids chemically or physically. Examples will be given below.

The microcrystals produced according to the invention, offer principally the advantage of being able to obtain a microsuspension stable in aqueous solution of a substance which is otherwise insoluble. This permits said substance to be administered, when it is a medicament, in injectable or sprayable form. Compared with liposomes, preparations in the form of microcrystals, according to the invention, are simpler and much more economical to prepare to the extent that they involve the presence of a reduced number of constituents. They are much more stable, whereas the instability of liposomes considerably limits their conditions of use.

In addition, apparently by virtue of an increased piloting effect particularly towards macrophages on the one hand, and a gradual release effect of the incorporated active substance, on the other hand, the microcrystal preparations give results of therapeutic activity and of toxicity which are also more advantageous than vesicles of the liposome type.

In general, according to the invention, phosphatidylcholine will preferably be used as the phospholipid. Phosphatidylcholine, however, can be used if necessary in combination with other known elements for example, in the preparation of liposomes, namely sterols like cholesterol or again stearylamine.

However, since the formation of microcrystals is concerned, the molar ratio of phospholipid to active substance is of determining influence. The molar ratio of phospholipid to sterol, for example, does not have an influence on the formation of microcrystals.

In certain cases however, it may be advantageous to add one or more sterols to reinforce the activity of the insoluble active substance to be incorporated.

The molar ratio of phospholipid to active substance must be less than that beyond which only liposome type vesicles are observed.

In fact, if the molar ratio of phospholipid to active substance used in the process according to the invention is too high, particularly higher than 10, for example, there is observed essentially the formation of lipid vesicles resembling liposomes.

On the other hand, if the molar ratio is less than or equal to 2, preferably close to 1, there is observed a specific interaction with the homogeneous production of microcrystals whose average size is between 0.1 and $1\mu$.

For intermediate ratios, mixtures of lipid vesicles and of microcrystals are obtained.

The molar ratio between the one or more phospholipid(s) and one or more sterol(s), as the case may require, like cholesterol, does not have a determining influence on the formation of microcrystals. However, in certain cases, it may be advantageous to add one or more sterol(s) to reinforce the activity of the active substance.

According to a modification of the process, step a of the process is subdivided thus:

a1) the one or more solvents are evaporated from a phospholipid solution, a2) the lipid film obtained after evaporation, is dissolved, by adding a solution of said substance thereto, and then a3) the one or more solvents of the phospholipid solution and said substance are evaporated.

In the process, the molar ratio between the one or more phospholipid(s) on the one hand, and said substance on the other hand, is preferably between 0.1 and 2 more preferably between 0.8 and 1-2, or again close to 1.

When a sterol is associated with the substance to be processed, the molar ratio in the process between the one or more phospholipid(s) and the one or more sterol(s) is preferably between 1 and 2.

To place the film obtained in step a) in suspension, various known techniques may be used, but it is advantageous to be able to use ultrasound processing.

In a particular embodiment of the invention, the solvents used are the usual organic solvents, such as chloroform or methanol or again solvent mixtures, for example, of chloroform and methanol.

For example, the phospholipid solution is a chloroform solution and the solution of the substance concerned is a solution of a chloroform/methanol mixture. The sterol solution, as the case may require, can be a methanol solution.

According to another characteristic of the process, the microcrystals are purified by centrifugation and washing with distilled water or with an aqueous solution.

The present invention relates, for example, to microcrystals comprising as active substance ginkgolides.

The best known of the ginkgolides are ginkgolides A, B, C and M which are used in therapy for the treatment and prevention of disorders caused by the PAF-acether as described in Belgian Pat. No. 901915. Among these compounds ginkgolide B shows itself to be particularly interesting.

Ginkgolide B is of very low solubility; this constitutes a drawback when it is desired to incorporate it in certain pharmaceutical compositions, in particular injectable compositions. Moreover it is interesting to have available pharmaceutical compositions capable of conveying the active substance up to the activity sites and thus to increase the specificity of the active substance whilst reducing as far as possible the undesirable effects.

It is an object of the present invention to resolve the problems discussed above with the novel crystalline form called "microcrystals".

In the particular case mentioned, the insoluble substances according to the invention will be selected from among ginkgolides and their derivatives and more particularly it relates to ginkgolide B. Although among the ginkgolides, ginkgolide B is preferred, it is also possible to use the derivatives, such as monoacetates, triacetates, and tetrahydro- or acetylated derivatives.

The ginkgolides are substances which take part in the treatment of disorders caused by the acether of the "platelet activating factor".

The acether of the "platelet activating factor" (PAF-acether) is a phospholipid which can be the cause of numerous maladies in the human being or in animals. The acether of the "platelet activating factor" causes the aggregation of the platelets, as well as the release of their basoactive amine. The release is caused in animals and human beings under the effect of different types of shock, such as anaphylactic shock, burns, septic shock, shock through irradiation and wounds. Its release leads subsequently to a suppression of immune reactions following the exhaustion of the defense means of the organism. In fact, since its identification (1-0-alkyl-2(R)-acetyl-glycero-3-phosphorylcholine) and its total synthesis, proofs of its participation in certain pathological processes have accumulated, principally, in pulmonary anaphylaxis and different states of shock.

Numerous specific antagonists of PAF-acether are known. Two series are principally to be distinguished:
1) Substances having a structure similar to that of PAF-acether,
2) Natural substances with a specific antagonistic activity.

Among the second category, are to be found on the one hand lignans and neolignans such as kadsurenone (*Piper futokadsurae*) magnosalicine (*Magnolia salicifolia*), nectandrins A and B (*Nectandra rigida*) and synthetic dinorlignan L-652,731 and, on the other hand, terpenoids isolated from *Ginkgo biloba* (Ginkgolides).

However, these antagonist substances of the acether of "the platelet activating factor" show a major drawback, in that they are very insoluble, which makes their use in fact almost non-existent since it is dependent in practice on administration by perfusion.

Quite surprisingly, it has been discovered according to the invention, that the ginkgolides may be rendered injectable by interacting with phospholipids in the form of microcrystals.

It is the same for other antagonist substances of the acether of the "platelet activating factor", which are hydrophobic substances and which interact with phospholipids. The majority of these substances are in fact observed on the one hand, to be hydrophobic and on the other hand, also show an affinity for the phospholipids and hence an aptitude for the formation of microcrystals with the phospholipids, these microcrystals constituting a microsuspension stable in aqueous solution.

The affinity of antagonist substances of the acether of "platelet activating factor" for phospholipids is doubtless the cause of their inhibiting action on PAF-acether which also has, as has been seen, a phospholipid structure. As has been discovered by applicants, this affinity offers the possibility of injecting these substances by the preparation of microcrystals. However, in addition it is possible that the similitude of the phospholipid structures on the one hand, of the microcrystals formed and, on the other hand, of the PAF-acether contributes also to greater therapeutic activity of the pharmaceutical compositions containing these microcrystals of antagonist substances of PAF-acether.

According to another example of the present invention, the active substance concerned may be selected from among antagonist substances of the acether of "platelet activating factor".

In this process, "antagonist substances of the acether of 'platelet activating factor'" means substances enabling the effective treatment of disorders caused by the acether of the "platelet activating factor".

More particularly, according to the present invention, antagonist substances of the acether of the "platelet activating factor" can be chosen from among synthetic products having a structure similar to that of "platelet activating factor" or natural products, such as terpenoids, lignans and neolignans.

Particularly, among lignans and neolignans, the antagonist substances of the acether of the "platelet activating factor" are selected from among kadsurenone, magnosalicine, nectandrins A and B and synthetic dinorlignane L-652,731.

Among the synthetic products, may be mentioned the derivatives of canthene 5, 6.

According to another example of the present invention, the active substance concerned may be selected from among amphotericin B and its derivatives having an antifungal activity. A description of certain of these compounds will be found in the literature [1].

Amphotericin B and its derivatives, particularly aminoacyl derivatives, continue to be medicaments of choice for the treatment of numerous deep fungal infections despite their severe toxicity and considerable unpleasant secondary effects.

It has already been proposed to reduce the toxicity and to increase the activity of amphotericin B by encapsulating it in liposomes. However, the results obtained, from this point of view, although positive, are still not sufficient.

The microcrystals of amphotericin B or of its derivatives enables these disadvantages of high toxicity to be alleviated, whilst increasing the antifungal activity of said substances, distinctly more effectively than the liposomes, apparently among other things by virtue of a piloting effect of the substance towards target cells like macrophages, as well as an improved effect of progressive release of the active substance. In addition, the process of preparation of microcrystals is generally simpler to perform than encapsulation in liposomes and the preparations obtained are more stable.

The preparation of microcrystals also permits amphotericin B to be injected without use of the deoxycholate as in FUNGIZONE ® (amphotericin B deoxycholate), the latter being toxic.

Amphotericin has an affinity for sterols, which is why, in one embodiment of the process according to the present invention, amphotericin B or one of its derivatives is supplemented with sterol(s), particularly cholesterol (Ch) or ergosterol.

According to another example of the present invention, the active substance is nystatin, which is an antifungal agent. Nystatin suffers from disadvantages similar to those of amphotericin B, including high toxicity and low solubility in water.

Advantageously in step b of the process, when the substance concerned is an anti-PAF-acether agent, the film obtained after evaporation of the solvent is suspended in a buffered solution at pH between 5 and 8, preferably at pH 5.9, for example, in an acetate or phosphate buffer.

In step b) of the process, when the substance is amphotericin B, particularly in the absence of sterol, the aqueous solution is, for example, an NaCl solution. In the presence of sterol, the aqueous solution of step b) of the process may be distilled water or NaCl. Then advantageously after step b) of the process, the microcrystals are purified by centrifugation and washing in an aqueous solution from step b.

It is also possible, particularly when the substance concerned is amphotericin B to advantageously use saccharide solutions, for example lactose or again glucose, particularly 0.1 M solutions, as the aqueous solution. The microcrystals obtained may, under these conditions, be freeze-dried. There results therefrom a possibility of long term preservation.

According to the present invention there are also provided the microcrystals obtained, and particularly microcrystal preparations which may be freeze-dried.

They are microcrystals of a substance insoluble in water having an affinity for phospholipids and at least one phospholipid in the molar ratio of phospholipid to insoluble substance of between 1-2 or again close to 1. The microcrystals have a size between 0.1 and $2\mu$, or more particularly, close to $0.5\mu u$.

The microcrystals according to the invention may include, for example, an insoluble substance selected from among ginkgolides and their derivatives and a phospholipid which may be phosphatidylcholine or one of its derivatives.

For example, microcrystals, characterised in that they comprise ginkgolide B and phosphatidylcholine in a substantially equimolecular ratio, may be mentioned.

More generally, the invention also relates to microcrystals containing an anti-PAF-acether agent and one or more phospholipid(s), preferably in a molar ratio close to 1.

In another example, the present invention relates to microcrystals containing amphotericin B or one of its antifungal derivatives.

In a particular embodiment, these microcrystals comprise amphotericin B or one of its derivatives, supplemented or not with sterol(s) and phosphatidylcholine.

For example, microcrystals comprising amphotericin B and phosphatidylcholine in a molar ratio close to 1.

In a further example, the present invention relates to microcrystals containing nystatin. For example, microcrystals of nystatin and phosphatidylcholine. Preferably, the molar ratio of phosphatidylcholine to nystatin is between 0.1 and 10, more preferably between 0.8 and 5, and most preferably between 0.8 and 1.4.

When a sterol is associated with the active substance, from the point of view of the molar ratio of the components incorporated in the microcrystals, the molar ratio of phospholipid to sterol and substance is between 0.8 and 1.4, or again close to 1.

Thus, there may be mentioned particularly the molar ratio of phosphatidylcholine: cholesterol: amphotericin B of 4:2:1, which is an overall molar ratio between the phospholipid and the substance to be treated supplemented with the sterol(s) of 4:3.

It is also an object of the present invention to provide pharmaceutical compositions comprising as active principles, microcrystals according to the present invention.

Preferably, these pharmaceutical compositions are formulated in injectable or sprayable form or again in freeze-dried form.

Other characteristics and advantages of the present invention will become apparent in light of the detailed description which follows in the form of examples.

DETAILED DESCRIPTION OF PREFERRED EMBODIMENTS

EXAMPLE 1

DEVELOPMENT OF ADMINISTRABLE FORMS OF GINKGOLIDE B

Ginkgolides A, B and C are terpenes isolated from the leaves of *Ginkgo biloba* and possessing an antagonist activity relative to the acether of the platelet activating factor, the phospholipid involved in inflammatory reactions and immediate hyposensitivity reactions (for example, platelet aggregation, bronchial spasm, ...).

The more active compound: ginkgolide B, has a solubility in water limited to 100 g/ml. On the other hand, the treatment or prevention of diseases caused by the acether of the platelet activating factor involves the administration of 1 to 50 mg of ginkgolide per kg namely for a man of 70 kg, between 70 and 3500 mg of ginkgolide B.

The problem of producing an administrable form of ginkgolide B hence arises. The molecular being very hydrophobic, it was first thought to coat the ginkgolide B in lipid vesicles (liposomes) and subsequently, a method for obtaining microcrystals of ginkgolide B associated with phosphatidylcholine has been developed giving the best results.

A) INCORPORATION IN LIPOSOMES

It was chosen first to incorporate it in multilamellar liposomes composed of phosphatidylcholine (PC), cholesterol (Ch) and stearylamine (SA).

The liposomes were prepared at pH 7.4, then at a slightly acidic pH.

1. Preparation of liposomes

Multilamellar liposomes containing ginkgolide B were prepared as follows.

The lipids: 50 $\mu$moles (39.25mg) of phosphatidylcholine (PC), 37.5 $\mu$moles (14.51 mg) of cholesterol (Ch) and 12.5 $\mu$moles (3.37 mg) of stearylamine (SA) were dissolved in 10 ml of chloroform/methanol (4:1 by volume) in a 500 ml flask. The ginkgolide B dissolves in the methanol added to (0.86 to 4.25 mg) namely 2–10 $\mu$moles) and the solvent was evaporated under vacuum by means of a rotary evaporator at a temperature of 30° C. The film was taken up again in 10 ml of chloroform and reevaporated to obtain a uniform lipid film in the flask.

The multilamellar liposomes (MLV) were formed by the addition of 4 ml of phosphate buffer pH 7.4, 0.15 M in NaCl and vigorous stirring at the vortex for 5 minutes and then left under nitrogen for 16 hours.

Effectiveness of the incorporation of the ginkgolide B in the liposomes MLV depends on the amount of ginkgolide B engaged and reaches, at pH 7.4, a maximum of 64%.

2. Liposomes prepared at pH 6.5

Ginkgolide B was incorporated in liposomes MLV composed of phosphatidylcholine, cholesterol and stearylamine (4:3:1) at pH 6.5 (phosphate buffer 0.15 M) following the same procedure as at pH 7.4, but by increasing the amount the ginkgolide B contacted with the lipids. The results indicate that the percentage incorporation reaches 87%, namely one molecule of ginkgolide B per 4.4 molecules of phosphatidylcholine.

3. Liposomes prepared at pH 5.9

Ginkgolide B (GB) was incorporated in liposomes MLV at pH 5.9 according to the same procedure as at pH 7.4. The results show that the percentage incorporation is improved further namely one molecule of GB per 2.8 molecules of PC. The better incorporation at pH 5.9 is explained doubtless by the greater stability of ginkgolide B at this pH, the opening of the lactone rings at neutral or alkaline pH, leading to more hydrophilic products being known. However, the stability of the liposomes is not improved.

B) PREPARATION OF MICROCRYSTALS OF GINKGOLIDE B

In addition to liposomes, the presence of stable microcrystals has been observed in a preparation whose molar ratio PC/GB was 1.54.

Observation of microcrystals in place of liposomes containing ginkgolide B has led to studying the conditions of their maximum production. First of all the influence on their formation of the lipid composition of liposomes and that of the ratio between the amount of phosphatidylcholine and ginkgolide B, was analyzed.

1. Microcrystals obtained from PC, Ch and SA

In a first stage, the proportions of phosphatidylcholine (PC), of cholesterol (Ch) and of stearylamine (SA) were varied. However, the molar ratios PC/GB are not similar and it emerges from the results, shown in table I below, that the ratio between the phosphatidylcholine and the cholesterol does not have a determining influence on the formation of microcrystals. On the other hand, the ratio PC/GB is essential and hence was studied in a second stage.

Preparations of the "liposome" type composed of PC:Ch:SA in a ratio (5:4:1) were obtained with a ratio PC/GB of 7.5 and more (preparation E-31). Examination by optical phase contrast microscopy shows that the preparation after sonification is constituted essentially of liposomes with rare microcrystals of the same size as the liposomes.

The influence of the ratio PC/GB on the formation of microcrystals containing ginkgolide B is set out in detail in Table II below for lipid mixtures composed of PC:Ch:SA in a molar ratio 4:3:1. It emerges therefrom that if the ratio PC/GB is higher than 7.5, the formation of lipid vesicles resembling liposomes is essentially observed whilst if the molar ratio is less than or equal to 2, preferably close to 1, there is observed principally microcrystals whose average size is between 0.2 and 0.7 μ. For intermediate ratios PC/GB, mixtures of liposomes and of microcrystals are obtained.

These microcrystals are much smaller than those obtained by treating ginkgolide B alone under the same conditions.

2. Toxicity

Aliquot parts of the preparations E-31 (liposomes) and E-34 (microcrystals) were preserved for an acute toxicity study in the mouse.

The preparation E-31 (liposomes) injected i.v. into mice at the dose of 13.1 and 25.9 mg/kg induces a loss in weight of 1.8 and 7.1% respectively after 12 days. On the other hand, the preparation E-34 (microcrystals) is only toxic at the dose of 48.9 mg/kg with mouse death 2 hours after injection i.v. whilst at 21.8 mg/kg, no toxicity is observed, on the contrary, a gain in weight of 24% after 12 days is observed.

EXAMPLE 2

PREPARATION OF MICROCRYSTALS GINKGOLIDE B BY PREFERENTIAL INTERACTION WITH PHOSPHATIDYLCHOLINE

The production of microcrystals by interaction between ginkgolide B and the constituents customarily used for the preparation of the liposomes has led to abstracting each time one of these constituents and determining the simplest way of preparing them. It appears that phosophatidylcholine is essential, but the presence of cholesterol and of stearylamine is not essential for the production of microcrystals, whence a great simplification of the process.

If microcrystals having a molar ratio PC/GB of 1.0 are prepared without cholesterol, small microcrystals are obtained of homogeneous size and shape. Microcrystals prepared in the same manner from PC and Ch, without SA and having a molar ratio of PC/GB of 1.0 have a tendency to aggregate and their average size is greater than 4 μ.

1. Microcrystals PC:GB

Finally, if the cholesterol and stearylamine are removed, only the phosphatidylcholine and the ginkgolide B remain. If the molar ratio PC/GB is greater than or equal to 2.0, only microcrystals are obtained.

As indicated in Table III below, if the molar ratio PC/GB is greater than 2.0, the presence of lipid microvesicles ("liposomes") is observed in the preparation, whose average size is greater than 1 μ. If the molar ratio PC/GB is less than 1.0, we observe a heterogeneous microcrystals population from the point of view of the size and shape but the average size is greater than the 1 μ.

For an equimolar ratio PC/GB, we obtain smaller microcrystals, of average size between 0.2 and 0.7 μ. Their formation results from a specific interaction between ginkgolide B and phosphatidylcholine.

PREPARATION OF MICROCRYSTALS AT pH 5.9 (E-35)

Microcrystals containing ginkgolide B (GB) are prepared from 0.10 mmoles of PC and 0.10 mmoles of ginkgolide B.

a) Preparation

The lipid film is formed in a 500 ml flask by dissolving 78.5 mg of PC in 10 ml of chloroform-methanol (4:1 in volume) and 42.5 mg of ginkgolide B in 50 ml of methanol and by evaporating the solvent under vacuum by means of a rotary evaporator at a temperature of 30° C.

The microcrystals are formed by the addition of 50 ml of acetate buffer 0.15 M pH 5.9 and sonification for 5 min. at 100 Watts in an ultra-sound bath. The microcrystals GB:PC are preserved under nitrogen at 4° C.

b) Purification

It emerges therefrom that preparations based on liposomes do not have an inhibiting effect on platelet aggregation essentially up to 1 hour 30 minutes only, whilst the effect of microcrystals was more prolonged at doses of 1 mg/kg administered i.v.

E-30=Liposomes (PC/Ch/SA)=(7/2/1) to 1.283 mg GB/ml

E-31=Liposomes (PC/Ch/SA)=(5/4/1)2.695 mg GB/ml

E-34=Microcrystals with 4.250 mg GB/ml buffer=acetate buffer pH 6.0; 0.15 M.

TABLE I

EFFECT OF THE LIPID COMPOSITION ON THE OBTAINING OF MICROCRYSTALS CONTAINING GINKGOLIDE B

| Composition | Molar Ratio (PC/GB) | Average size (nm) | Appearance in optical phase contrast microscopy |
|---|---|---|---|
| PC:Ch:SA (7:2:1) | 3.1* | N.D. | Round and elongated liposomes no microcrystals |
| PC:Ch:SA (4:3:1) | 1.25 | 634 nm | Microcrystals, little or no liposomes |
| PC:Ch:SA (5:4:1) | 7.5** | N.D. | Liposomes (95%) + some microcrystals |
| PC:Ch:SA (4:6:1) | 1.0 | >4000 nm | Elongated microcrystals + large crystals of cholesterol |

*preparation E-30
**preparation E-31
N.D. = Not determined

TABLE II

EFFECT OF THE MOLAR RATIO PC/GB ON THE OBTAINING OF MICROCRYSTALS CONTAINING GINGKOLID B

| Compostion | Molar Ratio (PC/GB) | Average size (nm) | Appearance in optical phase contrast microscopy |
|---|---|---|---|
| PC:Ch:SA (4:3:1) | 10.0 | N.D. | Essentially small liposomes |
| PC:Ch:SA (4:3:1) | 7.5 | N.D. | Round and elongated liposomes + rare microcrystals (1–5%) |
| PC:Ch:SA (4:3:1) | 5.0 | N.D. | Liposomes microcrystals (10–25%) |
| PC:Ch:SA (4:3:1) | 2.5 | N.D. | Microcrystals (50–70%) + liposomes |
| PC:Ch:SA (4:3:1) | 1.25 | 634 nm | Principally small microcrystals + rare liposomes (1–5%) |
| PC:Ch:SA (4:3:1) | 0.60* | 242 nm | Essentially microcrystals of ± homogenous size |

*preparation E-34

TABLE III

EFFECT OF THE MOLAR RATIO PC/GB ON THE OBTAINING OF MICROCRYSTALS CONTAINING GINKGOLIDE B

| Composition | Molar Ratio (PC/GB) | Average size (nm) | Appearance in optical phase contrast microscopy |
|---|---|---|---|
| PC:GB | 4.0* | 2100 | Liposomes + aggregates of liposomes Few microcrystals |
| PC:GB | 2.0 | 2200 | Mixture of small and aggregated liposomes and of microcrystals |
| PC:GB | 1.0** | 250 to 650 | Small microcrystals, no liposomes |
| PC:GB | 0.5 | 2970 | Small microcrystals and a heterogeneous population of larger crystals |
| PC:GB | 0.25*** | 3390 | Larger microcrystals, more elongated and of more irregular shape than for the molar ratio PC/GB 1.0 |

*preparation E-39
**preparation E-35
***preparation E-40

The preparation of microcrystals is centrifuged at 2000 g for 15 min. and the microcrystals are washed twice with doubly distilled water. The microcrystals in the water have the same microscopic appearance as those obtained in an acetate buffer at pH 5.9.

A suspension of microcrystals of ginkgolide B having a homogeneous size of the order of 500 mm at a concentration of ginkgolides of 12.8 mg/ml is obtained.

2) Anti-PAF-acether Activity

Ginkgolide B was compared with 2 preparations of liposomes containing ginkgolide B (preparation E-30 and E-31) as well as with a microcrystal preparation (preparation E-34) in ex vivo tests on the rabbit in percentage inhibition on platelet aggregation (PAF 2.5 nM).

3. Toxicity

The preparation E-35 of microcrystals GB:PC (molar ratio of 1.0) was injected i.v. into Balb/c mice of 22 grams. At the dose of 178.5 mg/kg, the maximum weight loss was 16.2% at day 3 then the mouse recovered its initial weight at day 8.

At the dose of 118.4 mg/kg, the weight loss continued and the mouse was dead at day 5. At doses of 56.6 and 28.4 mg/kg, no toxicity was observed, a gain in weight of 6 to 8% was even observed after 2 days at the lowest dose tried.

4. Stability of the GB miorocrystals

The preparation E-35 (ratio PC/GB of 1.0) was preserved under nitrogen at 4° C. for 100 days and examined under the optical phase contrast microscope, the day of their preparation, at days 7, 15, 20 and 100. At day 7, the population was relatively homogeneous with an average size a little greater than at day 1. At day 100, there was still observed small microcrystals, but also the presence of microcrystal clusters. The measurement of the average sizes by means of the nanosizer confirms the results. Between day 1 and day 20, the average size doubled and at day 100, it was about 2 μ.

The increase of the average size of the microcrystals therefore results from the slow formation of microcrystal aggregates whose individual sizes do not seem to increase in the course of time. This aggregate formation in the course of storage at 4° C. may be avoided by the addition of additives such as anti-oxidants or saccharides.

In conclusion, it is possible to obtain a relatively homogeneous population of ginkgolide B microcrystals, of size between 0.1 and 1 μ by specific and equimolar interaction of this anti-PAF-acether agent with amphiphile molecule like phosphatidylcholine. By optical microscopy, it seems that the microcrystal population is relatively homogeneous from the point of view of size and shape. In electron microscopy, these microcrystals are in the form of "pebbles" with rounded edges.

Without difficulty of preparation, a milky suspension can be obtained containing 12.8 mg of ginkgolide B per ml.

The toxicity of this preparation of microcrystals after i.v. administration in the mouse is low. The anti-PAF-acether activity of this preparation is verified.

Microcrystals are also obtained, if there are added in addition phosphatidylcholine, cholesterol and stearylamine (PC:Ch:SA; 4:3:1) provided that the molar ratio PC/GB is less than 2.

EXAMPLE 3

ANTI-PAF-ACETHER AGENTS

In the literature there will be found numerous other anti-PAF-acether agents which can be applied to the process according to the present invention, particularly in "PAF-acether specific binding sites: 2. Design of specific antagonists" of P. Braquet and J.J. Godfroid (Tips—Oct. 1986—Elsevier Science Publishers B.V., Amsterdam).

Several series of anti-PAF agents may be distinguished, among others, including:

1) Antagonists having a molecular structure similar to that of PAF-acether, such as CV-3988 (Takeda), RU-45703 (Roussel-Uclaf/Pharmacochimie Moleculaire), ONO-0240 (ONO), RO 19-3704 (Hoffman-La Roche, SRI 63-119 (Sandoz) and SRI 63-072 (Sandoz) or again antagonists having a structure modified with respect to that of PAF-acether such as Piperidine SRI 63-072 (Sandoz) or Dioxanone (Hoffmann-La Roche).

2) Natural products like lignans and neolignans such as kadsurenone (*Piper futokadsurae*) magnosalicide (*Magnolia salicifolia*), nectandrins A and B (*Nectandra rigida*) and synthetic dinorlignan L-652,731 of the formula:

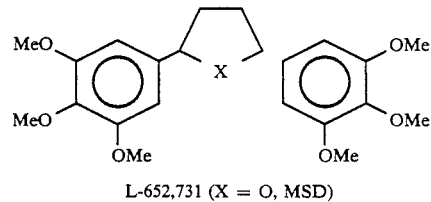

L-652,731 (X = O, MSD)

Besides the terpenoids isolated from Ginkgo biloba (ginkgolides) also concerned by the present application.

EXAMPLE 4

PREPARATION OF KADSURENONE MICROCRYSTALS AT pH 5.9

Microcrystals containing kadsurenone and phosphatidylcholine are prepared according to the following scheme.

a) Preparation

A lipid film is formed in a flask by dissolving phosphatidylcholine and kadsurenone in a solvent in equimolar amounts, and after evaporation of the solvent under vacuum by means of a rotary evaporator at a temperature of 30° C.

Thus, to one milligram of kadsurenone (1 mg/ml) in chloroform: methanol (1:1 by volume), in a 50 ml flask is added 4.6 ml of phosphatidylcholine (0.5 mg/ml) in chloroform: methanol (4:1 by volume).

The microcrystals are formed by the addition of 0.5 ml of acetate buffer 0.15 M pH 5.9 and sonification for 5 minutes at 100 W in an ultra-sound bath. The microcrystals are preserved under nitrogen at 4° C. In this way microcrystals having a substantially homogeneous size of the order of 500 nm are obtained.

b) Purification

The preparation of the microcrystals is centrifuged at 2000 g for 15 minutes and the microcrystals are washed twice with twice-distilled water. The microcrystals in the water have the same microscopic appearance as those obtained in acetate buffer at pH 5.9.

EXAMPLE 5

PREPARATION OF MICROCRYSTALS AT pH 5.9 CONTAINING

PRODUCTS L-652,731 (MSD)

Microcrystals containing phosphatidylcholine and product L-652,731 (MSD) were prepared according to the scheme described in the preceding example. To 1mg of the product L-652,731 are added 3.9 ml of phosphatidylcholine (0.5 mg/ml) in a 50 ml flask and the solvent is evaporated off under vacuum at 30° C.

The film is taken up again with 0.5 ml of 0.15 M acetate buffer, pH 5.9 and subjected to ultrasound for 5 minutes at power of 100 W.

EXAMPLE 6

PREPARATION OF AMPHOTERICIN B MICROCRYSTALS

Microcrystals containing amphotericin B and phosphatidylcholine in an equimolar ratio were prepared according to the following scheme:

a) Preparation: Into a 500 ml flask, are introduced 15.7 ml of phosphatidylcholine (99% pure egg lecithin) with 10 mg/ml of chloroform (0.2 mM). A lipid film is formed by evaporation of the solvent under vacuum by means of a rotary evaporator at a temperature of 30° C. Then 370 ml of amphotericin B is added to 0.5 mg/ml of chloroform-methanol mixture (1:1, by volume), namely 0.2 mM.

After evaporation of the solvent under vacuum by means of a rotary evaporator, the microcrystals are formed by addition of 10 ml of 9‰ NaCl and sonification for 15 min. in an ultra-sound bath JULABO model USR 6.

b) Purification: The preparation of microcrystals of amphotericin B is centrifuged for 2 minutes at 2000 g in a table centrifuge. The supernatant liquor is applied to the top of a Sepharose 6B column eluted by 9‰ NaCl. The fraction of the first peak most enriched in amphotericin B contained 8.23 mg of amphotericin B/ml and 7.1 mg of phosphatidylcholine/ml namely a molar ratio ampho/PC of 0.98.

c) Acute Toxicity in the Mouse: At the dose of amphotericin B of 82.2 mg/kg administered intravenously, the preparation of amphotericin B microcrystals is toxic with respect to OFI female mice, the death of the mouse taking place within 3 minutes following the injection. At the dose of 41.1 mg/kg the mouse injected intravenously was dead on the second day. On the other hand, at the dose of 20.6 mg/kg, the mouse injected intravenously lost about 20% of its weight during the 7 days following the injection and then recovered its weight at day 22.

Amphotericin in the form of FUNGIZONE (amphotericin B deoxycholate) administered intravenously at $LD_{50}$ of 1.2 mg/kg according to LOPEZ-BERESTEIN et al [2] of 2.3 mg/kg according to SZOKA et al [3] and of 5 mg/kg according to WRIGHT et al. [1]

The $LD_{50}$ of amphotericin B-liposomes intravenously varies from 4 to 19 mg/kg according to the composition of liposomes (SZOKA et al., op. cit.)

The acute toxicity of amphotericin B-phosphatidylcholine microcrystals, administered i.v. to NMRI mice, was compared with that of amphotericin B complexed with deoxycholate (FUNGIZONE ® and with that of liposomes composed of phosphatidylcholine, cholesterol and stearylamine (molar ratios=4:3:1) containing amphotericin B prepared according to the technique of example I-A)1.

The dose inducing death of 50% of the mice, 14 days after the single administration of the products ($LD_{50}$) is 2.5 mg/kg for free amphotericin B; 18.3 mg/kg for microcrystals PC: AMPHO B.

In the form of microcrystals, AMPHO B is hence 7.3 times less toxic than in the form of a complex with deoxycholate.

d) In vitro cytotoxicity: The in vitro cytotoxicity is determined by the reduction in reducing enzymatic activity with respect to MTT (tetrazolium salt) of murine J774-G8 macrophages incubated overnight in the presence of RPMI enriched with 10% of foetal calf serum and containing the products at various doses.

The cytotoxicity is expressed in the form of the micromolar concentration of amphotericin B which reduces by 50% the reducing enzymatic activity of the macrophages ($TOX_{50}$).

TABLE 1

| Cytotoxicity of the different formulations of amphotericin B. | |
|---|---|
| Product | $TOX_{50}$ (μM) |
| FUNGIZONE | 4.0 |
| Microcrystals PC: AMPHO | 132 |

TABLE 1-continued

| Cytotoxicity of the different formulations of amphotericin B. | |
|---|---|
| Product | $TOX_{50}$ (μM) |
| Freeze-dried and reconstituted microcrystals | 132 |
| Liposomes: AMPHO | 17 |

The single table indicates that in the form of microcrystals AMPHO B is 33 times less toxic in vitro with respect to macrophages etc than free AMPHO B and 7.7 times less toxic than in liposome form.

The lyophilization of the microcrystals in the presence of 0.1 M sucrose and their reconstitution did not modify the cytotoxicity of the latter.

e) Direct antifungal activity. ( i.e. in vitro activity on extracellular parasites): The activity of the microcrystals of amphotericin B was compared with that of control amphotericin B solubilized in DSMO then diluted in RPMI culture medium containing 10% of lipid -depleted serum. With respect to Candida albicans and Candida tropicalis, the MIC (minimum inhibiting concentration of the growth of the parasites in vitro) of the two forms of amphotericin B was identical and was between 0.05 and 0.1 μM (0.04 and 0.08 μg/ml).

The direct antifungal activity of amphotericin B in the form of FUNGIZONE, of microcrystals or of liposomes was also measured on the growth of Candida tropicalis in RPMI medium containing 20% of foetal calf serum. Inhibition of the growth after 16 h was observed for increasing concentrations of amphotericin B (14 concentrations ranging from 0.012 to 100 μM. The minimum inhibiting concentration (MIC) is the lowest concentration at which growth of Candida is observed.

The MIC of amphotericin B in the form of microcrystals B:PC or in the form of FUNGIZONE was identical (0.195 μM). On the other hand amphotericin B encapsulated in liposomes composed of phosphatidylcholine, cholesterol and stearylamine in a molar ratio 4:3:1, is 8 times less active than free amphotericin (1.56 μM).

Freeze-drying of the microcrystals of amphotericin B:PC in the presence of 0.1M sucrose does not affect the antifungal activity of the latter relative to extracellular fungi.

f) In vitro activity with respect to macrophages infected by Candida Tropicalis (relative to intracellular parasites):

The antifungal activity of amphotericin B relative to intracellular fungi is determined in vitro in the model of the line J-774-G8 of macrophages infected in the proportion of 1 Candida tropicalis per 10 macrophages. The macrophages were cultivated in RPMI medium containing 10 mM MES pH 7.2 supplemented with 10% decomplemented human plasma. The action of the medicaments was measured in LIMBRO dishes with 24 wells containing $10^5$ infected macrophages, adhering to the glass slides, and the range of concentrations tested varied from 0.048 μM to 100 μM.

The percentage of infected cells was determined after 16 h of coculture. On microscope slides, after MAY-GRUNWALT-GIEMSA dyeing, the total number of macrophages (NT) was counted as well as the number of macrophages infected with Candida (Ni). The percentage of infection was the ratio Ni/NT (X 100).

The concentration, expressed in uM, which reduces by 50% the intracellular infection ($IC_{50}$) was then determined.

The $IC_{50}$ of FUNGIZONE is 0.2 μM whilst that for the microcrystals was 0.1 μM, whereas the $IC_{50}$ of liposomes containing AMPHO B was 0.8 μM.

The microcrystals are hence at least as active as amphotericin B, both with respect to extracellular fungi and with respect to intracellular fungi.

g) Therapeutic index: The therapeutic index (TI), defined on the intracellular forms of Candida, is the ratio between the toxicity of the product for the macrophages, expressed by the $TOX_{50}$ and the therapeutic activity expressed by the $IC_{50}$, the dose reducing by 50% intracellular infection.

As illustrated in the table below, the therapeutic index of the microcrystals PC: AMPHO B is 66 times higher than that of free AMPHO B (in FUNGIZONE form) and 60 times higher than that of liposomes containing AMPHO B.

TABLE 2

Therapeutic index of the different formulations of amphotericin B.

| Product | $TOX^a$ $(M)^{50}$ | $IC^b$ $(M)^{50}$ | $TI^c$ | product TI FUNGIZONE |
|---|---|---|---|---|
| FUNGIZONE | 4.0 | 0.2 | 20 | 1.0 |
| Microcrystals PC: AMPHO B | 132 | 0.1 | 1320 | 66.0 |
| Lyophylized Microcrystals | 132 | 0.6 | 220 | 11.0 |
| Liposomes: AMPHO | 17.0 | 0.8 | 21.3 | 1.1 |

$^a TOX_{50}$: Concentration expressed in μMoles, which reduces by 50% the reducing enzymatic activity of macrophages relative to tetrazolium salts.
$^b IC_{50}$: Concentration, expressed in μMoles, which reduces by 50% the intracellular infection of macrophages J-774-G8 infected with *Candida tropicalis*.
$^c TI$: Therapeutic index; ratio between the $TOX_{50}$ and the $IC_{50}$.

EXAMPLE 7:

Preparation of microcrystals of amphotericin B containing cholesterol.

The association of amphotericin B with sterols was tested (WITZKE et al., [4]), in particular with cholesterol and ergosterol. The incorporation of sterol with liposomes containing amphotericin B reduces their toxicity (SZOKA et al., [3]).

The addition of cholesterol has the same effect on the microcrystals of amphotericin B whilst increasing their activity.

The microcrystals of amphotericin B containing phosphatidylcholine (PC) and cholesterol (Ch) were prepared according to the following scheme:

a) Preparation: In a 500 ml flask, are introduced 15.7 ml of phosphatidylcholine (PC) at 10 mg/ml $CHCl_3$ (0.2 mM), 370 ml amphotericin B at 0.5 mg/ml of chloroform-methanol (1:1 by volume), namely 0.2 mM, and 58 mg of cholesterol (Ch) dissolved in 10 ml of methanol (0.15 mM).

The solvent was evaporated under vacuum at 30° C. with the help of a rotary evaporator.

The microcrystals were formed by the addition of 10 ml of water and sonification for 15 min in a JULABO model USR 6 ultrasound bath.

b) Purification: The preparation was purified as in the example 6. The fraction of the first peak, richest in amphotericin B contains 2.55 mg AMPHO B/ml, 9.11 mg PC/ml and 1.93 Ch/ml, namely a molar ratio: PC/Ch/Amphotericin B of 4/2/1.

c) Acute toxicity in the mouse: At the dose 25.5 mg/kg of amphotericin B, administered intravenously to 2 female OFI mice, the preparation of microcrystals of amphotericin B containing cholesterol induces a maximum weight loss of 8% at day 6 in one mouse and a gain in weight of 9% at day 6 in the second mouse (on the average: no loss in weight). The average weight of the 2 mice at day 19 was 100% of the initial weight.

d) Direct antifungal activity: The antifungal activity of the control amphotericin B (DMSO and RPMI) and the preparation of amphotericin B microcrystals containing cholesterol were of the same order. The MIC was between 0.05 and 0.1 μM.

e) In vitro activity relative to infected macrophages: The MIC of the preparation amphotericin B microcrystals containing cholesterol was 0.1 μM whilst for amphotericin B dissolved in DMSO it was 0.4 μM. The amphotericin B in the form of microcrystals containing cholesterol is hence at least four times less toxic and four times more active on infected macrophages with respect to amphotericin B.

EXAMPLE 8

Preparation of Nystatin Microcrystals

Microcrystals of nystatin were prepared at different molar ratios of phosphatidylcholine to nystatin as follows:

Nystatin microcrystals at a molar ratio of 1:1

(a) Preparation: 46.2 ml of a solution of nystatin at a concentration of 1.0 mg/ml of methanol (51 μmol) and 50 ml phosphatidylcholine (99% pure) at a concentration of 0.8 mg/ml of methanol (51 μmol) are added into a 1-liter, round-bottomed flask.

After evaporation of the solvent under vacuum using a rotary evaporator (T<40° C.), a film formed on the walls of the flask. After addition of 5 ml of 0.9% Nacl, the microcrystals are formed by sonification for 15 minutes in a JULABO model USR6 ultrasonic bath.

(b) Purification: After molecular sieving on a Sepharose 6B column eluted with 0.9% Nacl, the nystatin microcrystals are recovered in the exclusion peak of the column, equivalent to 5.7% of nystatin and 20.0% of the phosphatidylcholine introduced, with a molar ratio PC/NYST of 3.6. The majority of the nystatin (89%) and of the phosphatidylcholine (77%) has remained at the top of the column, in the form of large particles with a molar ratio PC/NYST of 0.88.

The average size of the microcrystals eluted from the column is 0.26 μm, as determined in a nanosizer.

Nystatin microcrystals, Example B (a) Preparation: 47 ml of a solution of nystatin at a concentration of 1.0 mg/ml of methanol (51 μmol) and 50 ml of phosphatidylcholine (egg lecithin, 99% pure) at a concentration of 3.2 mg/ml of methanol (204 μmol) are introduced into a 500-ml round-bottomed flask. A liid film is formed by evaporation of the solvent under vacuum using a rotary evaporator at a temperature of 30° C.

The nystatin microcrystals are formed by adding 4 ml of 0.9% NaCl and sonification for 15 min. in a JULABO model USR6 ultrasonic bath.

(b) Purification: The suspension of microcrystals is appleid to the top of a Sepharose 6B column, eluted with 0.9% NaCl, and 2-ml fractions are collected. In each fraction, the nystatin is assayed by measuring the absorbance at 306 nm and the phosphatidylcholine is assayed colorimetrically in an ABBOTT analyzer.

The microcrystals emerge in the void volume of the column (fractions 8-12), and the free nystatin as well as the free phosphatidylcholine in fractions 18-22.

32% of the nystatin and 33% of the phosphatidylcholine are recovered in the first peak, in the form of microcrystals having a molar ratio PC/NYST of 4.3. The maximum concentration of nystatin (fraction 9) is 2.7 mg/ml.

BIBLIOGRAPHIC REFERENCES CITED IN THE SPECIFICATION

[1]: WRIGHT et al. The Journal of antibiotics 1982 Vol. 35 N.7 pp 911-914.
[2]: LOPEZ-BERESTEIN et al. The journal of infectious diseases Vol. 145, N.5, May 1983 pp 939-945.
[3]: SZOKA et al. Antimicrobial Agents and Chemotherapy, Mar. 1987, p. 421-429 Vol. 31, n-3.
[4]: WITZKE et al. Biochemistry 1984, 23, 1668-1674.

We claim:

1. Process for the preparation of lipidic microparticles of an active substance and at least one phospholipid, the microparticles having a crystalline appearance and being stable in suspension in aqueous solution, said process comprising the steps of:
   providing a solution of a phospholipid and an active substance in one or more organic solvents, said active substance being substantially insoluble in water and having an affinity for phospholipids;
   evaporating the one or more organic solvents from said solution of phospholipid and said active substance to produce a film; and then
   suspending the film in an aqueous solution by vigorous stirring to produce lipidic microparticles of crystalline appearnace,
   wherein the molar ratio between the phospholipid and the active substance is between 0.8 and 1.2.

2. Process according to claim 1 wherein the phospholipid is phosphatidylcholine.

3. Process according to claim 1, wherein the organic solvent is methanol, chloroform or a mixture thereof.

4. Process according to claim 1, wherein the step of providing the solution of the phospholipid and the active substance in the organic solvent comprises the substeps of:
   providing a phospholid solution comprising a phospholipid and one or more solvents;
   evaporating the one or more solvents from the phospholipid solution to produce a lipid film; and then
   dissolving the lipid film by adding thereto a solution of the active substance in one or more organic solvents.

5. Process according to claim 1, wherein the vigorous stirring is obtained by treatment with ultrasonic vibrations.

6. Process according to claim 4, wherein the one or more solvents of the phospholipid solution is chloroform or a mixture of chloroform and methanol.

7. Process according to claim 4, wherein the one or more organic solvents in the solution of said active substance is a mixture of chloroform and methanol.

8. Process according to claim 1, wherein said active substance is selected form the group consisting of substances antagonistic to the acether of the "platelet activation factor".

9. Process according to claim 8, wherein the active substance is selected from the group consisting of lignans and neolignans.

10. Process according to claim 8, wherein the active substance is selected from the group consisting of kadsurenone and synthetic dinorlignan L-652,731.

11. Process according to claim 8, wherein the active substance is selected from the group consisting of ginkgolides.

12. Process according to claim 1, wherein said active substance is selected from the group consisting of amphotericin B and its aminoacyl derivatives, having an antifungal activity.

13. Process according to claim 1, wherein the solution of the phospholipid and the active substance is supplemented with a sterol.

14. Process according to claim 13, wherein the molar ratio between the phospholipid and the sterol is between 1 and 2.

15. Process according to claim 10 or 11, wherein the film obtained by evaporation of the organic solvent is suspended in an aqueous solution buffered to a pH between 5 and 8.

16. Process according to claim 10 or 11, wherein the film obtained by evaporation of the organic solvent is suspended in an aqueous solution of acetate or phosphate buffer.

17. Process according to claim 12, wherein the aqueous solution is a solution of Nacl or of 0.1 M saccharide.

18. Process according to claim 1, further comprising the step of purifying the microparticles by centrifugation and washing with distilled water or an aqueous solution.

19. Lipidic microparticles of crystalline appearance comprising an active substance and at least one phospholipid, said active substance being insoluble in water and having an affinity for phospholipids,
   wherein the molar ratio of phospholipid to active substance is between 0.8 and 1.2.

20. Microparticles according to claim 19, wherein a phospholipid is phosphatidylcholine.

21. Microparticles according to claim 19, wherein the active substance is an anti-PAF-acether agent.

22. Microparticles according to claim 19 wherein the active substance is selected from the group consisting of ginkgolides.

23. Microparticles according to claim 19, wherein the active substance is selected from the group consisting of kadsurenone and synthetic dinorlignane L652,731.

24. Microparticles according to claim 19, wherein the active substance is selected from the group consisting of amphotericin B and its aminoacyl anti-fungal derivatives.

25. Microparticles according to claim 19, further comprising a sterol.

26. Microparticles according to claim 25 wherein the molar ratio of phospholipid to active substance and sterol is between 0.8 and 1.4.

27. Microparticles according to claim 19, consisting essentially of amphotericin B, cholesterol and phosphatidylcholine in a molar ratio of 1:2:4 respectively.

28. Microparticles according to claim 19, wherein the microparticles are in freeze dried form.

29. Pharmaceutical composition comprising microparticles according to claim 19 as the active ingredient thereof.

30. Pharmaceutical composition according to claim 29, which is a liquid administrable by injection or as a spray.

31. Pharmaceutical composition according to claim 29, which is in freeze-dried form.

32. Process according to claim 1, wherein said active substance is nystatin.

33. Microparticles according to claim 19, wherein the active substance is nystatin.

34. Microparticles according to claim 33, consisting essentially of nystatin and phosphatidylcholine.

* * * * *